(12) United States Patent
Pianowski et al.

(10) Patent No.: US 9,713,601 B2
(45) Date of Patent: Jul. 25, 2017

(54) INGENOL DERIVATIVE COMPOUNDS AND METHODS USEFUL FOR INHIBITING CANCER CELL VIABILITY AND TREATING CANCER

(71) Applicant: AMAZÔNIA FITOMEDICAMENTOS LTDA., Fortaleza (BR)

(72) Inventors: Luiz Francisco Pianowski, Bragança Paulista (BR); Everardo Ferreira Telles, Fortaleza (BR)

(73) Assignee: AMAZÔNIA FITOMEDICAMENTOS LTDA, Fortaleza-CE (BR)

( * ) Notice: Subject to any disclaimer, the term of this patent is extended or adjusted under 35 U.S.C. 154(b) by 0 days.

(21) Appl. No.: 15/094,686

(22) Filed: Apr. 8, 2016

(65) Prior Publication Data

US 2016/0287544 A1    Oct. 6, 2016

Related U.S. Application Data

(62) Division of application No. 14/439,927, filed as application No. PCT/BR2013/000455 on Oct. 31, 2013, now abandoned.

(30) Foreign Application Priority Data

Nov. 1, 2012 (BR) ..................... 10 2012 028120 1

(51) Int. Cl.
| | |
|---|---|
| *A61K 31/22* | (2006.01) |
| *A61K 31/216* | (2006.01) |
| *C07C 69/618* | (2006.01) |
| *C07C 69/013* | (2006.01) |
| *A61K 31/23* | (2006.01) |
| *A61K 45/06* | (2006.01) |

(52) U.S. Cl.
CPC ............ *A61K 31/216* (2013.01); *A61K 31/22* (2013.01); *A61K 31/23* (2013.01); *A61K 45/06* (2013.01); *C07C 69/013* (2013.01); *C07C 69/618* (2013.01)

(58) Field of Classification Search
USPC ......................................... 514/163, 511, 654
See application file for complete search history.

(56) References Cited

FOREIGN PATENT DOCUMENTS

WO    WO2012/085189 A1 *  6/2012  ........... A61K 31/215

* cited by examiner

*Primary Examiner* — Pancham Bakshi
(74) *Attorney, Agent, or Firm* — B. Aaron Schulman, Esq.; Stites & Harbison, PLLC

(57) ABSTRACT

The present invention relates to new ingenol derivative compounds for inhibiting cancer cell viability and treating cancer. In other aspects, the invention relates to a pharmaceutical composition, a medicament, methods for treating cancer, and a dosage form.

5 Claims, 4 Drawing Sheets

INGENOL DERIVATIVE COMPOUNDS AND METHODS USEFUL FOR INHIBITING CANCER CELL VIABILITY AND TREATING CANCER

CROSS REFERENCE TO RELATED APPLICATIONS

The present application is a divisional application of U.S. Ser. No. 14/439,927, filed Apr. 30, 2015, which is the 371 application of International Application Serial No. PCT/BR2013/000455, filed Oct. 31, 2013, all of said applications incorporated herein by reference.

FIELD OF THE INVENTION

The present invention generally relates to new ingenol derivative compounds useful for treating cancer. In other aspects, the invention relates to pharmaceutical composition, medicament, use, method for treating cancer and dosage form.

BACKGROUND OF THE INVENTION

Cancer is the name given to a group of more than 100 diseases that have, in common, the disorganized growth of cells that invade tissues and organs, and which may spread to other regions of the body, in what is called metastasis.

Different types of cancer correspond to various cell types of the body. For example, there are several types of skin cancers, since the skin comprises more than one cell type. If the cancer starts in epithelial tissues, such as skin or mucosa, it is called carcinoma. If it starts in connective tissues, such as bones, muscles or cartilage, it is called sarcoma. Other characteristics that differentiate one type of cancer from others are the speed of cell multiplication and their ability to invade tissues and organs, in the vicinity or distantly from its origin.

The difficulty for the effective treatment of cancer relates to establishing the distinction between malignant and normal cells of the body. Both are derived from the same source and are very similar, and for this reason, there is no significant recognition by the immune system as to the threat. Until now, cancer can be treated by surgery, chemotherapy, radiotherapy and immunotherapy (monoclonal antibody therapy). The choice of treatment depends on the location, tumor grade and stage of the disease, as well as the general condition of the patient. The complete removal of the tumor without damage to the rest of the organism is the main goal of the treatment. Sometimes, this can be achieved through surgery, but the propensity of the disease to invade adjacent tissues or to spread to distant sites (metastasis) often limits its effectiveness. The chemotherapy effectiveness is, in most cases, limited by its toxicity to other tissues (cells) of the organism, as well as radiotherapy, which can also damage normal tissues. In immunotherapy, carcinogenic cells developed mechanisms to escape from the immune response, a phenomenon known as resistance to treatment.

DESCRIPTION OF THE FIGURES

The figures described below refer to $IC_{50}$ values obtained by exposing human tumor lines to the compounds of the invention.

DETAILED DESCRIPTION OF THE INVENTION

Figure 1:
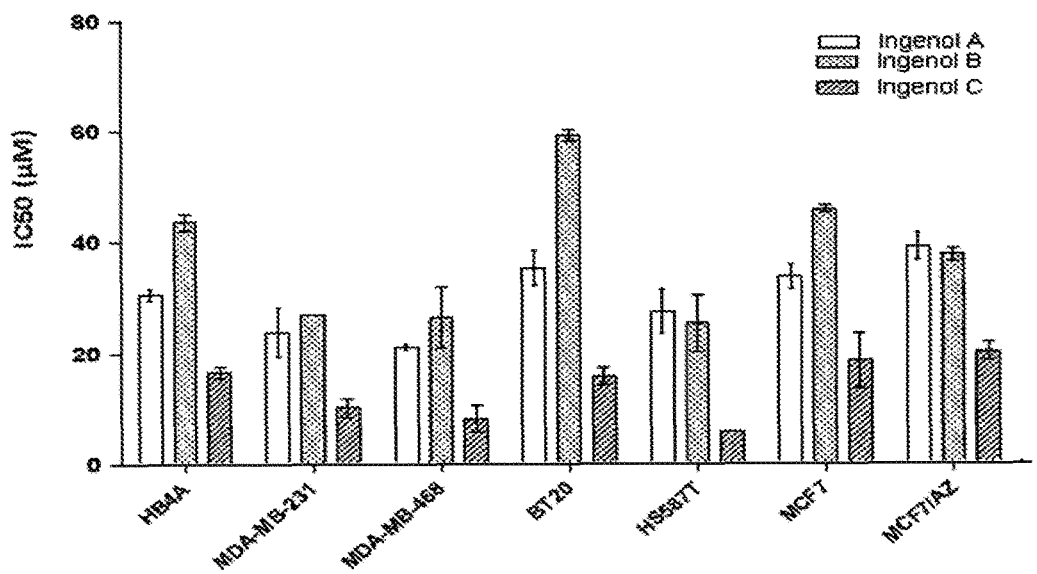
FIG. 1—HB4A, MDA-MB-231, MDA-MB-468, BT20, HT587T, MCF7 and MCF7/AZ lines, related to breast cancer.
Figure 2:
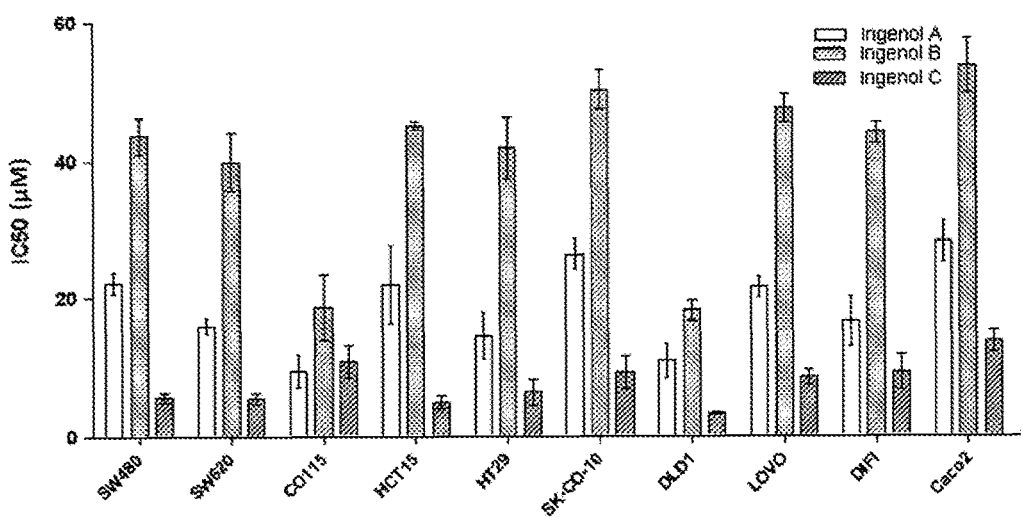
FIG. 2—SW480, SW620, CO115, HCT15, HT29, SK-CO-10, DLD1, LOVO, DIFI and Caco2 lines, related to colorectal cancer.
Figure 3:
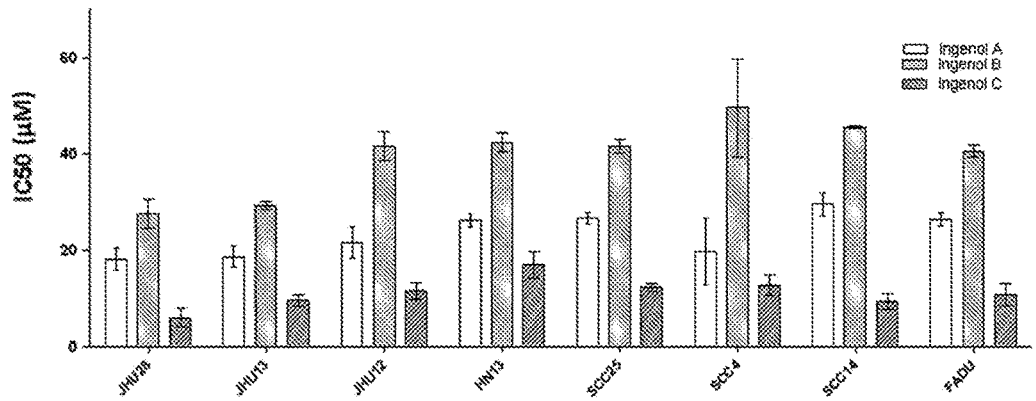
FIG. 3—JHU28, JHU13, JHU12, HN13, SCC25, SCC4, SCC14 and FADU lines, related to neck and head cancer.
Figure 4:
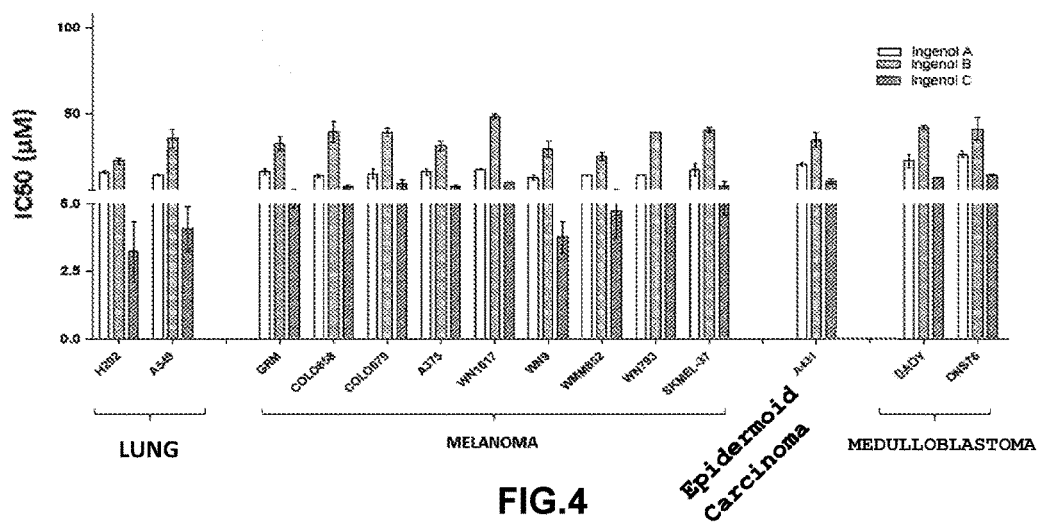
FIG. 4—H292 and A549 lines, related to lung cancer; GRM, COL0858, COLO679, A375, WN1617, WN9, WMM852, WN793 and SKMEL37 lines, related to melanoma; A431m line, related to epidermoid carcinoma; and DAOY and ONS76 lines, related to medulloblastoma.
Figure 5:
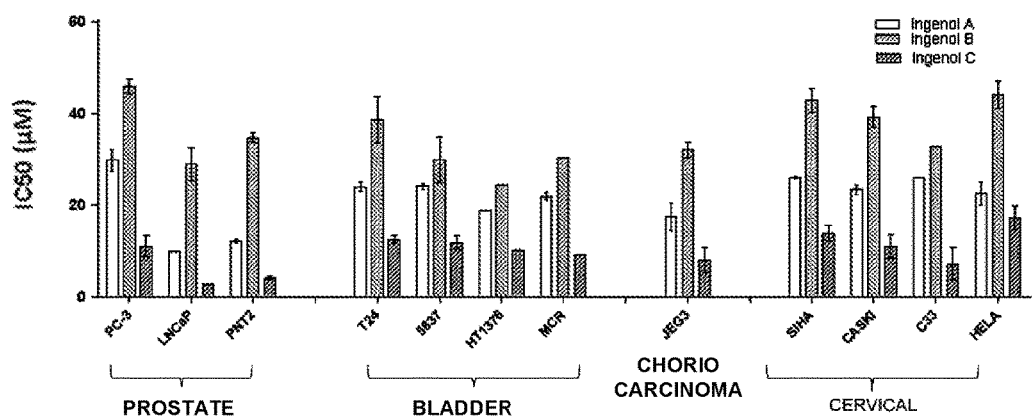
FIG. 5—PC-3 LNCaP and PNT2 lines, related to prostate cancer; T24, 5637, HT1376 and MCR lines, related to bladder cancer; JEG3 line, related to choriocarcinoma; SIHA, CASKI, C33 and HELA lines, related to cervical cancer.
Figure 6:
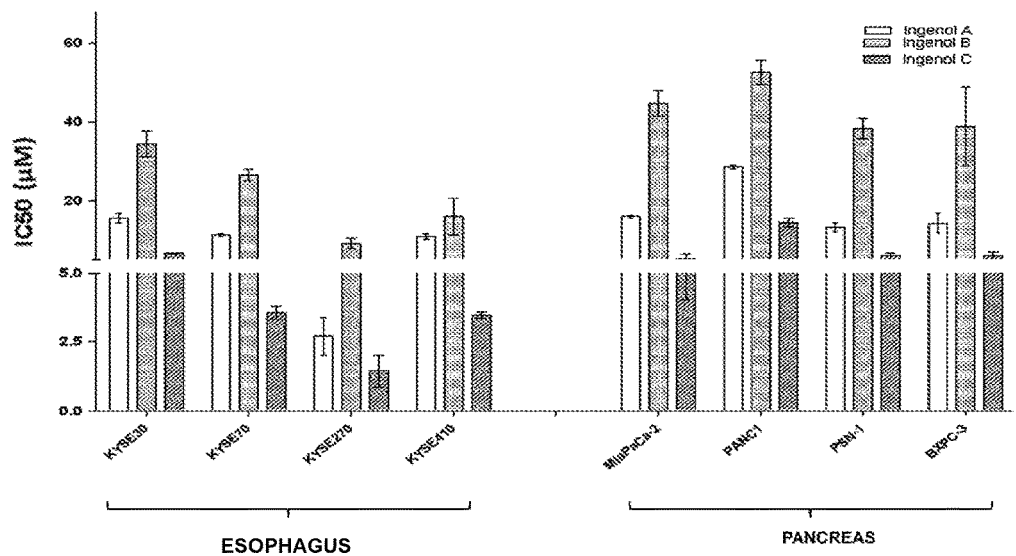
FIG. 6—KYSE30, KYSE70, KYSE279 and KYSE410 lines, related to esophageal cancer; MiaPaCa-2, PANC1, PSN-1 and BXPC-3 lines, related to pancreatic cancer.
Figure 7:
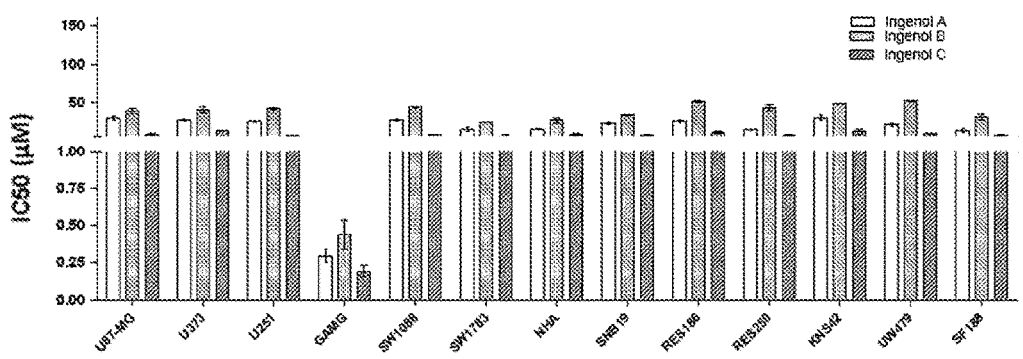
FIG. 7—U87-MG, U373, U251, GAMG, SW1088, SW1783, NHA, SNB19, RES186, RES259, KNS42, UW479 and SF188 lines, related to gliomas.
Figure 8:
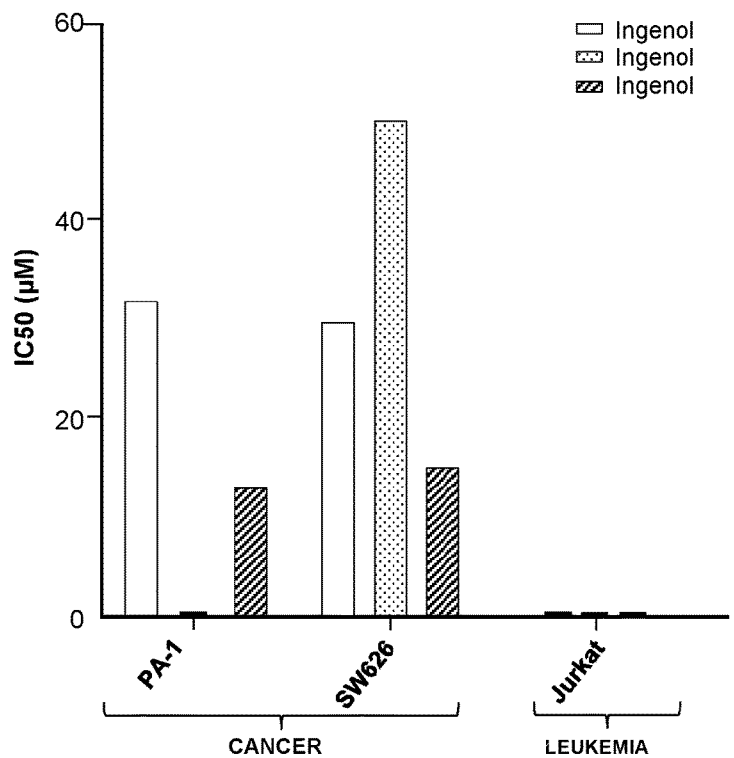
FIG. 8—Jurkat line, of leukemia, and PA-1 and SW626 lines, related to ovarian cancer.

The search for new ways to treat cancer is a process in constant progress, and within this dynamic, new active principles were developed to be useful in the treatment of cancer, combined with low toxicity.

In a first aspect, the present invention related to compounds derived from ingenol, of formula I

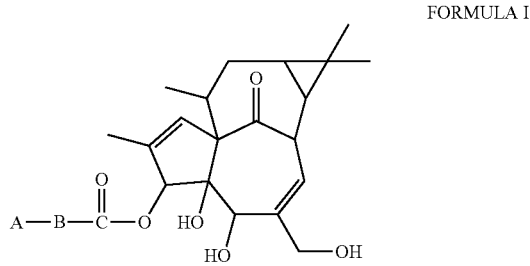

FORMULA I where
A is phenyl, $CH_3$— or $CH_2$=CH—,
And B is —CH=CH—, [—$CH_2$-]$_x$ or [—$CH_2$-]$_y$,
wherein x is an integer ranging between 1 and 10, preferably between 2 and 6, and y is an integer ranging between 1 and 10, preferably between 8 and 10,
provided that:
when A is phenyl, B is —CH=CH—;
when A is $CH_3$—, B is [—$CH_2$-]$_x$;
when A is $CH_2$=CH—, B is [—$CH_2$-]$_y$,
for treating cancer.

Particularly, and without excluding other alternatives, the ingenol derivative compounds of the invention are suitable for the treatment of breast cancer, colorectal cancer, head and neck cancer, brain cancer (for example, glioma and medulloblastoma), prostate cancer, bladder cancer, choriocarcinoma, cervical cancer, leukemia, skin cancer (for example, epidermoid carcinoma and melanoma), esophageal cancer, pancreatic cancer and ovarian cancer.

Particular examples of ingenol derivatives suitable to the invention, in a non-limited sense, are:

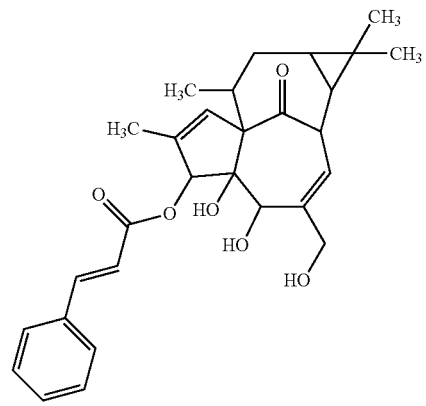

3-cinnamyl-ingenol

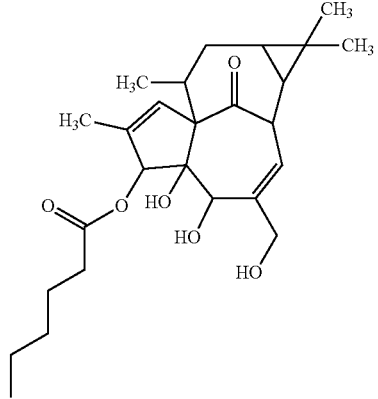

3-hexanoyl-ingenol

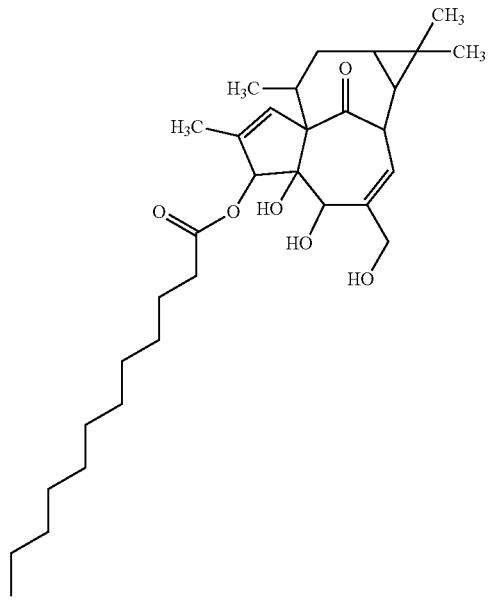

3-dodecanoyl-ingenol

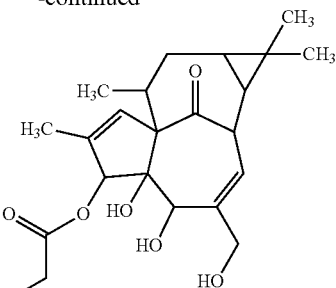

3-dodeca-11-enoyl-ingenol

Products derived from the invention, particularly those illustrated above, stand out for the low potential to generate toxic degradation products after metabolism.

Formula I encompasses isomers of the structures herein illustrated, as well as their pharmaceutically active derivatives, for example, salts, prodrugs, metabolites, crystals, hydrates and solvates.

Pharmaceutically active derivatives are those which typically exhibit a behavior similar to the free base molecule.

Pharmaceutically acceptable salts of the compounds of formula I are within the pharmaceutically active derivatives. A particular counterion, which is part of any salt of a compound of the invention, typically does not present critical nature, provided that the salt as a whole is pharmacologically acceptable and provided that the counterion does not contribute to undesirable qualities of the salt as a whole.

Without excluding any other, acid addition salts can be cited as pharmaceutically acceptable salts, such as inorganic salts, for example, hydrochloric, hydrobromic, sulfuric, nitric and phosphoric acids, or organic salts, for example, of acetic, propionic, hexanoic, heptanoic, glycolic, pyruvic, lactic, malonic, succinic, malic, maleic, fumaric, tartaric, citric, benzoic, cinnamic, methanesulfonic, p-chlorobenzenesulfonic, 2-naphthalenesulphonic, p-toluenesulfonic, camphorsulfonic, trimethyl acetic, t-butyl acetic, lauryl sulfuric, gluconic, glutaric, hydroxy naphthoic, salicylic, stearic, muconic, mandelic and 2-hydroxyethane sulfonic acids.

Without excluding any other, basic addition salts can be cited as pharmaceutically acceptable salts, such as ammonium salts, alkali metal salts, such as sodium, potassium, lithium, calcium or magnesium, salts with organic bases, such as salts of primary, secondary or tertiary amines (for example, isopropylamine, trimethyl amine, diethyl amine, triisopropylamine, tri-n-propylamine, ethanolamine, 2-dimethylaminoethanols, tromethamine, dicyclohexylamine, N-methyl-D-glucamine and salts with amino acids, such as arginine, lysine, histidine, caffeine, procaine, hydrabamine, choline, betaine, ethylenediamine, glucosamine, theobromine, purine, morpholine, etc. In some possible embodiments, the nitrogen-containing basic groups can be quaternized with alkyl halide-type agents, such as methyl, ethyl, propyl or butyl chlorides, bromides and iodides; long-chain halides, such as decyl, lauryl, myristyl and stearyl chlorides, bromides and iodides.

Ingenol derivatives of the invention can be prepared by different ways known to a person skilled in the art, by synthetic or semi-synthetic processes, for example, from plant raw materials (such as the active fraction resulting from the chromatographic separation of a butanolic extract from *Euphorbia tirucalli* L. latex, described in the international patent application WO2007000618), or from any other appropriate raw materials, for example, free base ingenol, terpenes, etc.

In another aspect, the present invention relates to pharmaceutical compositions comprising one or more compounds of formula I, and one or more pharmaceutically acceptable excipients. The term "pharmaceutically acceptable excipients" relates to inert substances used in pharmaceutical compositions as diluents, vehicles or additives without medicament activity per se. The following publications can be cited as information sources on such excipients: "Remington: The Science and Practice of Pharmacy", 20$^{th}$ Edition or later, Lippincott, Williams and Wilkins publishing house; "Pharmaceutical Dosage Forms and Drug Delivery Systems (1999) H. C. Ansel et al., 7$^{th}$ edition, Lippincott, Williams & Wilkins Publishing House; "Handbook of Pharmaceutical Excipients" (2000) A. H. Kibbe et al, 3$^{rd}$ edition, American Pharmaceutical Association Publishing House.

The ingenol derivatives of the invention, and the compositions containing them can be administered to a human or animal (non-human) patient by any appropriate route, for example, oral, parenteral, intravenous, intra-arterial, intraperitoneal, transdermal, sublingual, rectal, intramuscular, transbuccal, intra-nasal, liposomal, inhalation, vaginal, subcutaneous, intra-adipose, intraocular, intra-articular or intrathecal route, by using a catheter or stent, etc.

There are no particular restrictions regarding the dosage forms containing the ingenol derivative compounds of the invention. For example, tablets lozenges, capsules, granules, pellets and the like can be used for solid oral administration. For liquid oral administration, solutions, dispersions, suspensions, emulsions, oils, etc., can be used. Other appropriate dosage forms are liposomes and nanoparticles, or any other form known to a person skilled in the art. The dosage form may be of immediate, sustained or controlled release.

The term "liposome" means small vesicles consisting of one or more concentric phospholipids bilayers which spontaneously arrange themselves in an aqueous medium. They can be used as medicament controlled release systems. Liposomes can protect active principles from chemical, physical and enzymatic degradation, enable the increase of drug concentration in the target site, can be used as not-toxic excipients to solubilize hydrophobic drugs and may extend the lifetime of vesicle and drug in the circulation, generating positive effects on the characteristics of pharmacokinetics and toxicity of the active principle.

The term "nanoparticles" means ultra-thin particles, typically from 1 to 100 nanometers in diameter that can encapsulate or protect active principles or drugs and potentially present advantageous properties when used as a controlled drug release system. The nanoparticles may protect the active principle from chemical, physical or enzymatic degradation, enable an increase of drug concentration in the target site, can be used as not-toxic excipients to solubilize hydrophobic drugs and may extend the lifespan of the drug in circulation, producing positive effects on pharmacokinetics and toxicity of the active principle.

In a particular aspect, the composition of the invention comprises, in addition to one or more ingenol derivative compounds of formula I, at least one additional active principle different from the same, for example, chosen among an anti-tumor agent, anti-retroviral agent, antibiotic, anti-tumor agent, anti-cachexia agent, neurological agent, anti-diabetic agent, anti-hypertensive agent, proton pump inhibitors, etc.

The expression "active principle" means a biologically active substance.

In another aspect, the invention relates to a medicament comprising one or more ingenol derivative compounds of formula I.

In another aspect, the invention relates to the use of one or more ingenol derivative compounds of formula I in the preparation of a product useful for the treatment of cancer. In yet another particular aspect, the invention relates to a method for treating cancer, characterized in that one or more ingenol derivative compounds of formula I are administered to a patient, as such or in the form of a composition.

In yet another particular aspect, the invention relates to the use of one or more ingenol derivative compounds of formula I for treating cancer.

In yet another particular aspect, the invention relates to a dosage form for treating cancer, characterized by containing between 0.01 and 5000 mg of one or more ingenol derivatives of formula I, according to claim 1. An adequate dosage for treatment, according to the invention, can be administered at once, or several times over time.

EXAMPLES

Particular examples of embodiments of the invention are given below, relating to some ingenol derivatives, without intending in any way to limit the invention to only such examples.

In the examples that follow the following ingenol derivatives of formula I, illustrated below, were used, herein named ingenol A, ingenol B and ingenol C, for ease of reference. It is to be noted that there are indications of stereospatial conformation for each compound.

INGENOL A

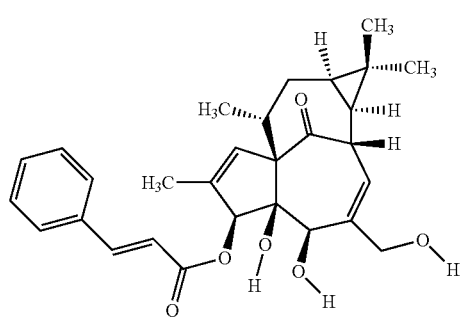

INGENOL B

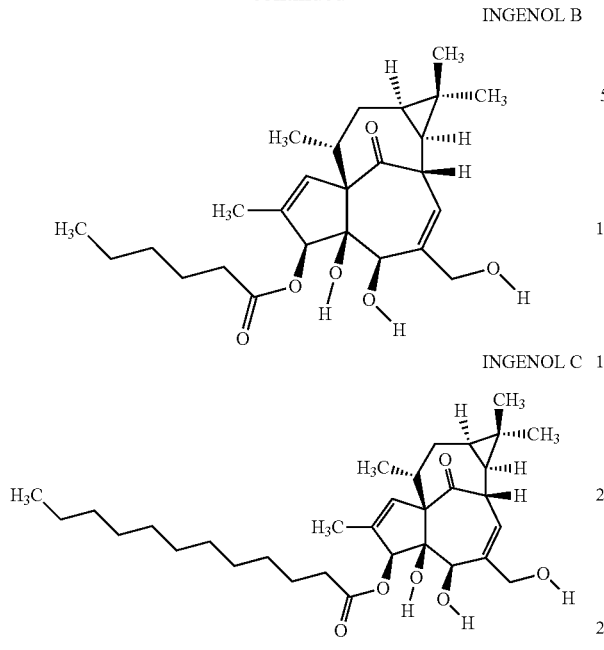

INGENOL C

Example 1

Several cancer cell lines were tested in vitro—the test is described below—to determine the 50% inhibitory concentration ($IC_{50}$), which is the concentration required to inhibit 50% of the cell activity, in μm (micromol).

Preparation of the Cells Used in the Tests

The cancer cells tested were grown in DEMEM medium (Dulbecco's Modified Eagle Medium) or RPMI medium (Roswell Park Memorial Institute) 1640, both supplied by the American company Life Technologies, supplemented with 10% fetal bovine serum (Life Technologies) and 1% penicillin/streptomycin (Life Technologies) in culture vials of 25 or 75 cm², of polyethylene or in culture plates, with average density of $1\times10^6$, at 37° C., 5% $CO_2$ and 90% humidity, until confluence was reached. After confluence, the cells were trypsinized (0.05% trypsin solution/0.53 mM EDTA—TripLE Express product, Life Technologies), plated and kept under the conditions described above for the tests that follow.

$IC_{50}$ Determination.

A cell viability assay in aqueous solution was used for this determination, using the product "*Cell Titer 96 Aqueous One Solution Cell Proliferation Assay*", supplied by the American company Promega, described by the manufacturer as a colorimetric method to determine the number of viable cells in the proliferation or cytotoxicity assays. CellTiter 96 contains the tetrazolium compound [(3-(4,5-dimethyl-2-yl)-5-(3-carboxymethoxyphenyl)-2-(4-sulfophenyl)-2H-tetrazolium, inner salt; MTS] and an electron coupling reagent (phenazine ethosulfate; PES). PES has an improved chemical stability, which allows its combination with MTS to form a stable color solution. The absorbance measured at different test and control samples allows determining whether the number of living cells in each sample is similar. For this assay, $3\text{-}5\times10^3$ cells were seeded in 96 well plates, in triplicate, and dilutions of the compounds of the invention (0; 2.5; 5; 7.5, 10 and 20 μM—diluted in DMSO—dimethyl sulfoxide) were added thereto. Dilutions of the compound were made so that the cells were subjected to only 1% DMSO/well. The absorbance was measured with an ELISA plate reader (Flash Varioskan equipment, supplied by the American company Thermo Scientific) at 490 nm after 72 hours of treatment. Data was collected and normalized in relation to the average survival of samples treated only with DMSO (considered 100% of viability). The experiments were carried out in experimental and biological triplicates.

The results of the absorbance values were converted into percentage of cell viability, wherein cells in the presence of the vehicle (DMSO) were used as control, corresponding to 100% of survival. The non-linear regression analysis using the program Graphpad Prism (supplied by the American company Graphpad Software) was conducted on the feasibility results, resulting in the equation used to calculate the concentration of the substance required to produce 50% of reduction of cell viability ($IC_{50}$).

As can be seen in FIGS. 1 to 8, the ingenol derivative compounds, according to the invention, have anti-cancer activity, demonstrated in the in-vitro $IC_{50}$ tests (50% of the Maximum Inhibitory Concentration) for a large number of cancer lines.

Figure 9:
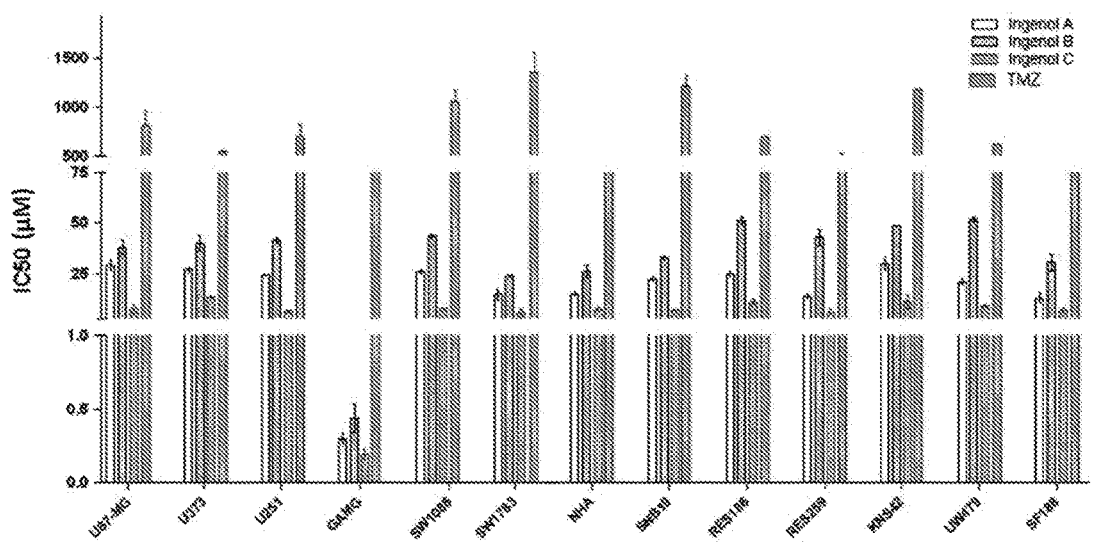
FIG. 9—some cancer cell lines, compared with the value obtained with temozolomide compound (indicated as TMZ), a drug used in the treatment of brain cancer.

As can be seen in FIG. 9, the products of the tests conducted with ingenol derivatives of the invention, in comparison with temozolomide, an antitumor product used in the oncology clinic for treating brain cancer, were more potent and effective.

Example 2

Process of obtaining ingenol from the active fraction resulting from chromatographic separation of a latex butanolic extract from *Euphorbia tirucalli* L. (hereinafter ingenol pool), described in the international patent application WO2007000618.

A hydrolysis reaction was carried out with 18 g of ingenol pool eluted in 300 mL of methanol and 6 mL of sodium methoxide. The reaction was monitored by HPLC analysis every 30 minutes at 214 and 290 nm in YMC Pro C18, 4.6×50 mm, 3 μm column, with A-B gradient of 5-70% in 7 minutes, at 1.5 mL/min. Solvents: solvent A—0.1% TFA in water, solvent B—0.08% TFA in acetonitrile.

The reaction was neutralized with 1 ml of glacial acetic acid. The subsequent purification was conducted in a 75% ethyl acetate solution in heptane applied in a flash column containing 300 g of silica. The column was balanced with the same solvent. Ingenol was eluted in 100 g of ethyl acetate. Elution was monitored with a UV detector at 290 nm. The combined fractions were evaporated.

Example 3

Preparation of Ingenol-5,20-Acetonide Intermediate, to Protect Hydroxyl Groups 5 and 20

A reaction was conducted for ingenol acetonide formation in 7.34 g of hydrolyzed ingenol from example 2 (1.00 equiv; 21.1 mmol) eluted in 250 mL of acetone (34.1 volEquiv) with 76.0 mg of (1S)-(+)-10-camphor sulfonic acid (C2107; 0.0104 weightEquiv; 99%). The reaction was monitored by HPLC analysis every 15 minutes at 214 and 290 nm in YMC Pro C18, 4.6×50 mm, 3 μm column, with A-B gradient of 5-70% in 7 minutes, at 1.5 mL/min. Solvents: solvent A—0.1% TFA in water, solvent B—0.08% TFA in acetonitrile. After 1.5 h reaction, 78% 5,20-ingenol acetonide and 9.8% ingenol were detected. The reaction was neutralized with 140 μL of triethylamine (47.9 mEq; 1.01 mmol).

Purification of 5,20-ingenol acetonide was conducted by evaporation at 35° C./30'/10 Torr, followed by crystallization from toluene.

Example 4

Esterification of 5.20 acetonide of example 3, followed by deprotection of the intermediate obtained, to prepare ingenol 3-dodecanoate (ingenol C).

Ingenols A and B, mentioned earlier, as the person skilled in the art knows, can be prepared in a manner similar to that described in this example, using, instead of dodecanoic acid, cinnamic anhydride or acid (for ingenol A) and caproic acid or anhydride (for ingenol B).

Esterification 3.60 g of 5,20-ingenol acetonide (1.00 equiv; 9.27 mmol) produced according to example 3, were eluted in 80 mL acetonitrile (22.2 volEquiv) with 4.17 g of dodecanoic acid (1.50 equiv; 13.9 mmol, and 4.53 g of cesium carbonate (1.50 equiv; 13.9 mmol).

The reaction was monitored by HPLC analysis every 15 minutes at 214 and 290 nm in YMC Pro C18, 4.6×50 mm, 3 μm column, with A-B gradient of 5-70% in 7 minutes, at 1.5 mL/min. Solvents: solvent A—0.1% TFA in water, solvent B—0.08% TFA in acetonitrile.

The obtained intermediate, 5,20-isopropylidene-ingenol-3-dodecanoate, was then subjected to extraction and purification.

Extraction of the product of this step of the synthesis in dichloromethane and water was performed. The organic phase was dried with magnesium sulfate and evaporated at 35° C./30'/10 Torr. This was followed by purification through solubilization in 5% ethyl acetate in heptane, and then applied in a flash column containing 80 g of silica. The column was balanced with the same solvent. Thereafter, the column was washed with 5% ethyl acetate in heptane solution. The intermediate 5,20-isopropylidene-ingenol-3-dodecanoate was eluted in 10% ethyl acetate in heptane solution. Elution was monitored by HPLC with UV detector at 290 nm. The combined fractions were evaporated at 35° C./30'/10 mbar.

Deprotection

For deprotection of the intermediate structure, 4.90 g of 5,20-isopropylidene-ingenol-3-dodecanoate (1.00 equiv, 8.29 mmol; 96%) were eluted in 80 mL methanol (19.9 volEquiv) with 4.60 mL of IN hydrochloric acid (1 M; 0.555 equiv; 4.60 mmol). This was followed by extraction with toluene and water. The organic phase was dried with magnesium sulfate and evaporated at 35° C./30'/10 Torr.

Ingenol 3-dodecanoate ingenol was obtained with purity of nearly 97%.

A person skilled in the art can readily evaluate, by means of the teachings contained herein, the advantages of the invention, and will know how to propose modifications and equivalent alternatives to the embodiments that were not expressly described without departing from the scope of the invention, as defined in the attached claims.

What is claimed is:

1. A method of inhibiting cancer cell viability comprising contacting said cancer cell with an ingenol derivative compound of formula I:

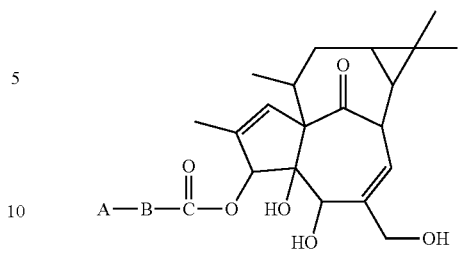

FORMULA I wherein A is $CH_3$— or $CH_2$=CH—, and B is —CH=CH—, [—$CH_2$-]$_x$ or [—$CH_2$-]$_y$,
where x is an integer ranging between 1 and 10,
where y is an integer ranging between 1 and 10,
provided that:
when A is $CH_3$—, B is [—$CH_2$-]$_x$; and
when A is $CH_2$=CH—, B is [—$CH_2$—]$_y$
or its crystals, hydrates, solvates, or pharmaceutically acceptable salts thereof;
wherein said cancer cell is selected from the group consisting of breast cancer cells, colorectal cancer cells, head and neck cancer cells, brain cancer cells, prostate cancer cells, choriocarcinoma cells, cervical cancer cells, leukemia cells, skin cancer cells, lung cancer cells, esophageal cancer cells, pancreatic cancer cells, bladder cancer cells, and ovarian cancer cells.

2. The method of inhibiting cancer cell viability according to claim 1, wherein x varies between 2 and 6 and y varies between 8 and 10.

3. The method of inhibiting cancer cell viability according to claim 1, wherein the compound is selected from the group consisting of 3-hexanoyl-ingenol, 3-dodecanoyl-ingenol, 3-dodeca-11-enoyl-ingenol, and combinations thereof.

4. The method of inhibiting cancer cell viability according to claim 1, wherein the compound is:

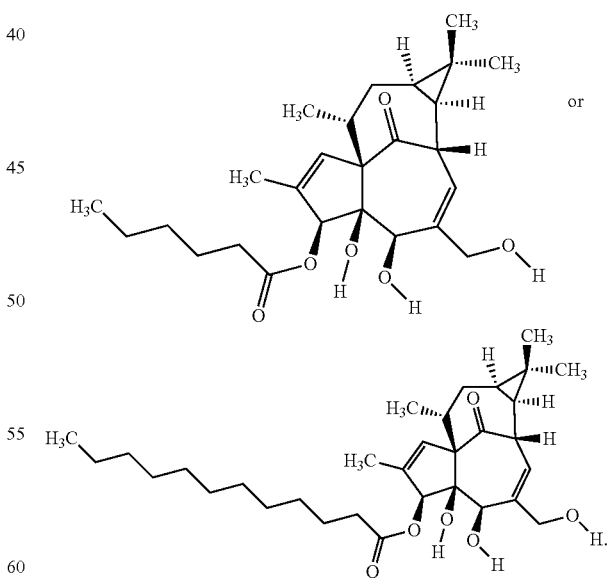

5. A method of inhibiting cancer cell viability according to claim 1 wherein the cells are contacted with the compound of formula I and one or more pharmaceutically acceptable excipients.

* * * * *